United States Patent
Suzuki et al.

(10) Patent No.: US 9,513,229 B1
(45) Date of Patent: Dec. 6, 2016

(54) PARTICLE MEASUREMENT MASK AND PARTICLE MANAGING METHOD

(71) Applicant: Kabushiki Kaisha Toshiba, Minato-ku (JP)

(72) Inventors: Masaru Suzuki, Kuwana (JP); Hiroyuki Mizuno, Kuwana (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 14/880,451

(22) Filed: Oct. 12, 2015

(30) Foreign Application Priority Data

Jul. 13, 2015 (JP) ................... 2015-139924

(51) Int. Cl.
*G01J 1/42* (2006.01)
*G01N 21/94* (2006.01)
*G01N 21/95* (2006.01)

(52) U.S. Cl.
CPC .......... *G01N 21/94* (2013.01); *G01N 21/9501* (2013.01); *G01N 2201/062* (2013.01); *G01N 2201/10* (2013.01)

(58) Field of Classification Search
CPC .... G01N 15/0656; G03F 7/70908; G03F 7/20; H01L 21/0274; H01L 22/12
See application file for complete search history.

(56) References Cited

U.S. PATENT DOCUMENTS

| | | | |
|---|---|---|---|
| 2002/0197545 A1* | 12/2002 | Ina | G03F 1/22 430/5 |
| 2005/0225308 A1* | 10/2005 | Orvek | G01N 15/0656 324/71.4 |
| 2016/0225610 A1* | 8/2016 | Chien | H01L 21/0274 438/16 |

FOREIGN PATENT DOCUMENTS

| | | |
|---|---|---|
| JP | 8-220009 | 8/1996 |
| JP | 2000-221138 | 8/2000 |
| JP | 2001-159613 | 6/2001 |

* cited by examiner

*Primary Examiner* — Kiho Kim
(74) *Attorney, Agent, or Firm* — Oblon, McClelland, Maier & Neustadt, L.L.P.

(57) ABSTRACT

According to one embodiment, a particle measurement mask includes a first mask substrate, a support member, and a particle measurement unit. The support member is arranged at a peripheral edge portion of a second main face of the first mask substrate, which is opposite to a first main face of the first mask substrate to come into contact with a mask stage. The particle measurement unit is arranged on a side surface of the support member, and configured to measure presence and absence of particles near the second main face.

20 Claims, 9 Drawing Sheets

PARTICLE MEASUREMENT MASK AND PARTICLE MANAGING METHOD

CROSS-REFERENCE TO RELATED APPLICATIONS

This application is based upon and claims the benefit of priority from Japanese Patent Application No. 2015-139924, filed on Jul. 13, 2015; the entire contents of which are incorporated herein by reference.

FIELD

Embodiments described herein relate generally to a particle measurement mask and a particle managing method.

BACKGROUND

Along with scaling of semiconductor devices, shortening of the wavelength of light sources used for light exposure apparatuses is progressing. Nowadays, a light exposure apparatus (EUV light exposure apparatus) using extreme ultraviolet light having a wavelength of about 100 nm or less (Extreme Ultraviolet Light: which will be referred to as EUV light, hereinafter) is becoming applied to manufacturing of semiconductor devices. Since EUV light is attenuated in the atmosphere, light exposure using the same is performed in a vacuum chamber, in general. Accordingly, an EUV light exposure apparatus of the mainstream type uses an electrostatic chuck to hold the rear face of a mask.

In the case of the type using an electrostatic chuck to hold the rear face of a mask, the contact area between the rear face of the mask and the holding mechanism tends to increase, as compared with a type using a vacuum chuck. This increases the possibility that, when particles are deposited onto the rear face of the mask or the holding mechanism, the particles are sandwiched therebetween. As a result, the height of the mask is partly changed, and its position for transferring patterns onto a wafer ends up being shifted. Further, if particles are deposited onto the face of the mask including light exposure patterns thereon, the particles are transferred as patterns, and pattern defects are thereby generated.

As described above, if particles are deposited onto the mask used in the EUV light exposure apparatus, they will have great influence on the light exposure. However, conventionally, there is proposed an apparatus for examining the presence and absence of foreign substances deposited on a test substrate, but there is not proposed a mechanism for monitoring particles deposited on a mask in an EUV light exposure apparatus.

DETAILED DESCRIPTION

In general, according to one embodiment, a particle measurement mask includes a first mask substrate, a support member, and a particle measurement unit. The support member is arranged at a peripheral edge portion of a second main face of the first mask substrate, which is opposite to a first main face of the first mask substrate to come into contact with a mask stage. The particle measurement unit is arranged on a side surface of the support member, and configured to measure presence and absence of particles near the second main face.

Exemplary embodiments of a particle measurement mask and a particle managing method will be explained below in detail with reference to the accompanying drawings. The present invention is not limited to the following embodiments. The perspective views, top views, and sectional views of a particle measurement mask used in the following embodiments are schematic, and so the relationship between the thickness and width of each member and/or the size ratios between respective members may be different from actual states.

First Embodiment

Figure 1A:
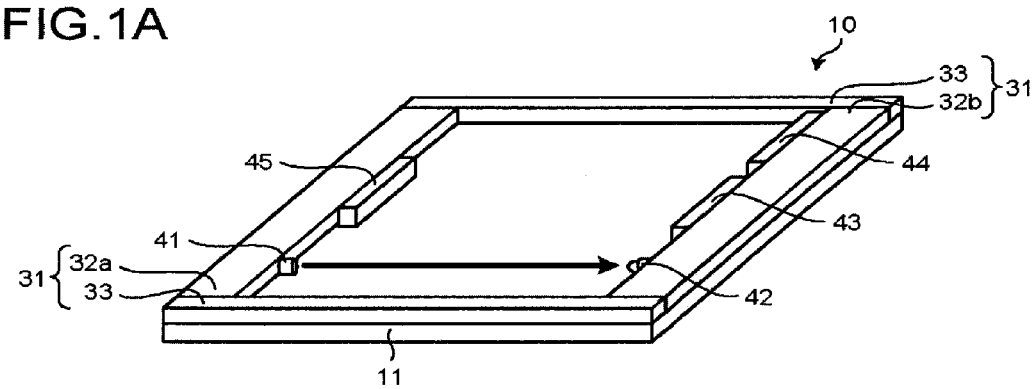
FIGS. 1A to 1C are views schematically showing an example of the structure of a particle measurement mask according to a first embodiment.
Figure 1B:
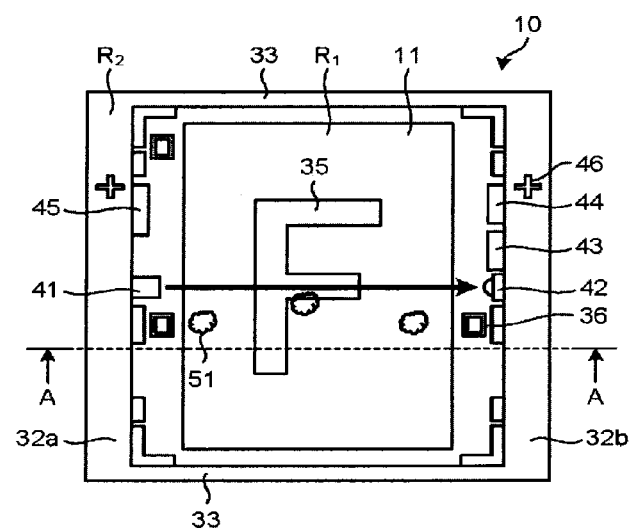
Figure 1C:
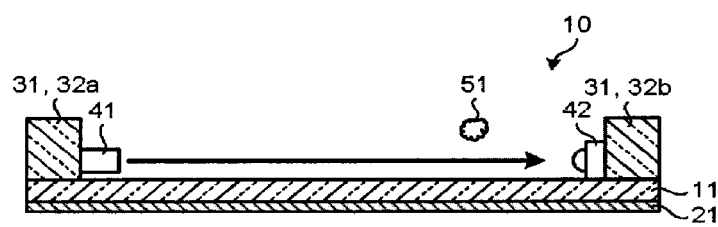

FIGS. 1A to 1C are views schematically showing an example of the structure of a particle measurement mask according to a first embodiment. FIG. 1A is a perspective view, FIG. 1B is a top view of FIG. 1A, and FIG. 1C is a sectional view taken along a line A-A of FIG. 1B. The particle measurement mask 10 is a mask having a function of measuring suspended particles inside a mask casing for storing a mask and inside a light exposure apparatus that uses a mask. The particle measurement mask 10 has the same size as a mask used in lithography for manufacturing ordinary products (which will be referred to as a product mask, hereinafter), and so it can be stored in a mask casing for storing the product mask. Hereinafter, this mask is exemplified by a particle measurement mask 10 to be used in an EUV light exposure apparatus.

The particle measurement mask 10 has a structure such that the front face of a mask substrate 11 is provided with a mechanism that can detect particles and a space that can detect particles, and the rear face is provided with an electrostatic chuck conductive film 21 for forming an electrostatic chuck mechanism that can hold the particle measurement mask 10. As the electrostatic chuck conductive film 21, for example, a CrN film is used.

The front face of the mask substrate 11 includes a pattern arrangement region $R_1$ and a peripheral region $R_2$. The peripheral region $R_2$ is disposed at the peripheral edge portion of the mask substrate 11. In the pattern arrangement region $R_1$, a main pattern 35, which is used for forming a device or the like to be constituted on a processing object, is arranged, and an auxiliary pattern 36, such as an alignment mark, is further arranged.

On the front face of the pattern arrangement region $R_1$, a multi-layered reflection film and a protection film are stacked in the order. The multi-layered reflection film reflects exposure light. As the multi-layered reflection film, for example, a multi-layered film composed of a plurality of stacked Mo/Si films may be used. The protection film protects the Mo films forming the multi-layered reflection film from oxidation. As the protection film, for example, Si is used.

On the protection film, an absorption layer is disposed. The absorption layer is made of a material having a low reflection coefficient to the exposure light. Accordingly, the absorption layer absorbs the exposure light. As the absorption layer, for example, a nitride containing tantalum and boron (TaBN) is used. The absorption layer has been patterned in a predetermined shape.

The peripheral region $R_2$ is provided with a frame member 31 arranged along the peripheral edge portion of the mask substrate 11. With the frame member 31, the upper surface of the peripheral region $R_2$ becomes higher than the pattern arrangement region $R_1$. Here, the frame member 31 is composed of first members 32a and 32b, which are portions arranged in directions parallel with the mask scanning direction in the light exposure apparatus, and second members 33, which are portions arranged in directions perpendicular to the mask scanning direction. Further, each of the first members 32a and 32b and second members 33 includes a surface arranged on the pattern arrangement region $R_1$ side, which will be referred to as an inner surface. On the front face of each of the first members 32a and 32b is provided with an alignment mark 46 for performing alignment. The frame member 31 may be formed of a different member from the mask substrate 11 and connected thereto by a connection member, or may be formed of the same member as the mask substrate 11 and shaped integrally therewith.

In the first embodiment, the inner surfaces of the first members 32a and 32b are provided with a mechanism that can detect particles. More specifically, the inner surfaces of the first members 32a and 32b are provided with a light emitting element 41, a light receiving element 42, an acceleration measurement unit 43, a logging unit 44, and a power supply 45.

The light emitting element 41 serves as a light source used for detecting particles 51 suspended over the front face of the particle measurement mask 10. As the light emitting element 41, for example, a laser diode or LED (Light Emitting Diode) may be used.

The light receiving element 42 is arranged opposite to the arrangement position of the light emitting element 41, and is configured to receive light emitted from the light emitting element 41. The light receiving element 42 outputs a received light intensity signal to the logging unit 44. As the light receiving element 42, for example, a photo diode or the like may be used.

The light emitting element 41 and the light receiving element 42 serve as a mechanism for detecting particles. During the measurement, the light emitting element 41 emits measurement light having a predetermined intensity toward the light receiving element 42, and the light receiving element 42 receives the measurement light. A reference received light intensity is defined by a light intensity of the measurement light received by the light receiving element 42 in a state where no particles 51 are present. During the measurement, if the received light intensity becomes smaller than the reference received light intensity, by a predetermined ratio or more, it is judged that particles 51 are present.

The acceleration measurement unit 43 serves as an accelerometer for measuring acceleration in the mask scanning direction, for example. The acceleration measurement unit 43 provides materials to make a later judgment as to whether or not it is during the mask scanning. The acceleration measurement unit 43 measures acceleration in the mask scanning direction at predetermined time intervals, and outputs the measurement result to the logging unit 44. Here, the acceleration measurement unit 43 measures acceleration in the mask scanning direction, but may be configured to measure acceleration in the three axial directions. Since this acceleration measurement unit 43 is used, the position of the particle measurement mask 10 can be specified during its transfer.

The logging unit 44 obtains the received light intensity signal from the light receiving element 42 and the acceleration from the acceleration measurement unit 43, and stores them. For example, the logging unit 44 logs the received light intensity signal in real time, and logs the acceleration at predetermined intervals. The logging data includes the elapsed time from starting the measurement, as well as the received light intensity signal and the acceleration, for example. The logging unit 44 and the light receiving element 42 are connected to each other by a signal line, and the logging unit 44 and the acceleration measurement unit 43 are connected to each other by a signal line.

The power supply 45 supplies electric power to the light emitting element 41, the light receiving element 42, the acceleration measurement unit 43, and the logging unit 44. Accordingly, although not shown, the power supply 45 is connected to the light emitting element 41, the light receiving element 42, the acceleration measurement unit 43, and the logging unit 44, by power supply lines.

In the example shown in FIGS. 1A to 1C, the inner surface of the first member 32a is provided with the light emitting element 41 and the power supply 45, and the inner surface of the first member 32b is provided with the light receiving element 42, the acceleration measurement unit 43, and the logging unit 44. Further, as described above, the light emitting element 41 and the light receiving element 42 are arranged opposite to each other.

Next, an explanation will be given of a particle managing method according to the first embodiment. The particle measurement mask 10 according to the first embodiment can measure particles 51, not only inside the light exposure apparatus but also inside a mask casing for storing a product mask. Accordingly, hereinafter, the structure of the mask casing will be briefly explained at first, and then the particle managing method will be explained.

Figure 2A:
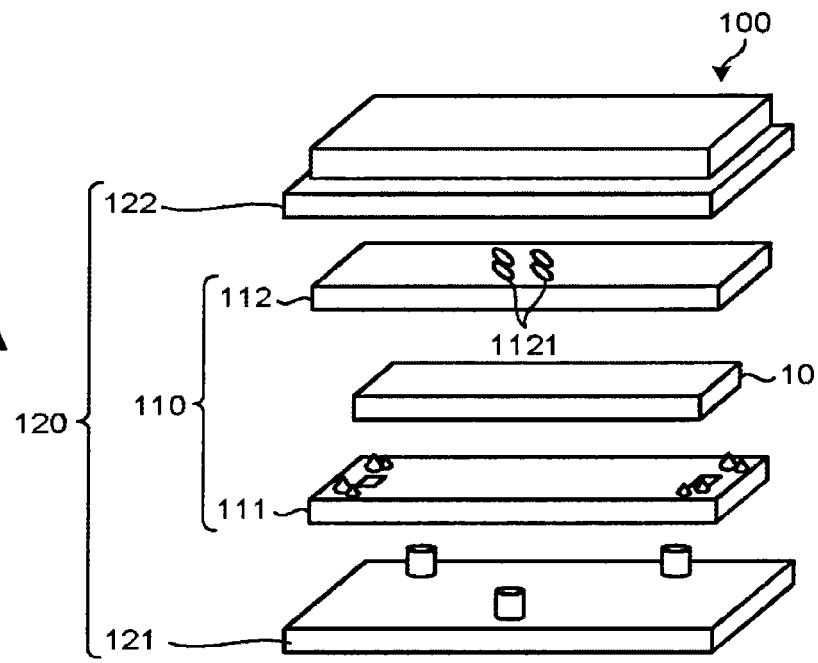
FIGS. 2A to 2C are exploded views showing the basic configuration of a mask casing.
Figure 2B:
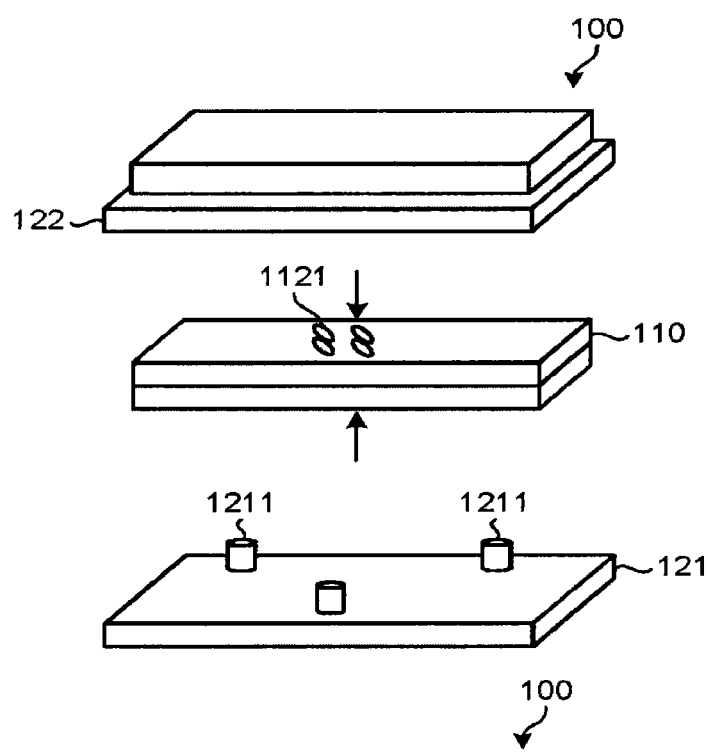
Figure 2C:
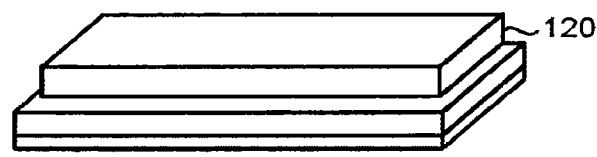
Figure 3A:
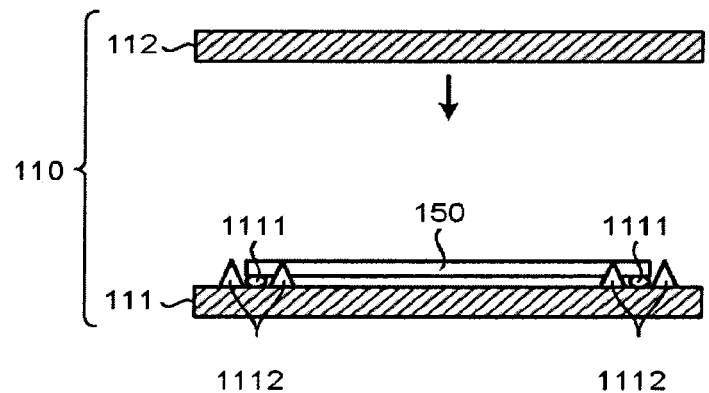
FIGS. 3A to 3C are views schematically showing an example of the configuration of an inner pod.
Figure 3B:
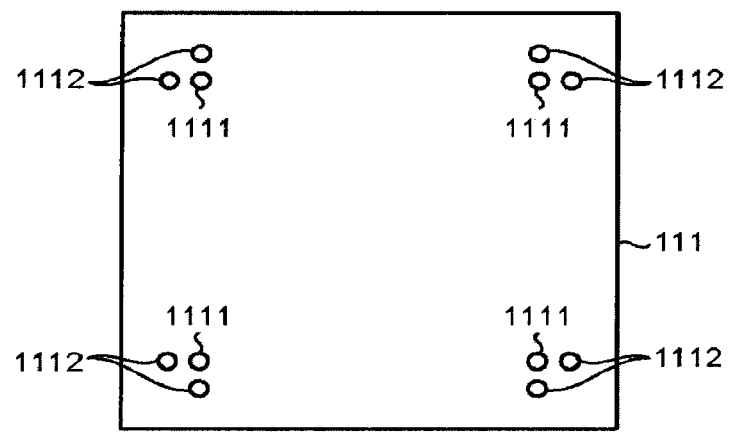
Figure 3C:
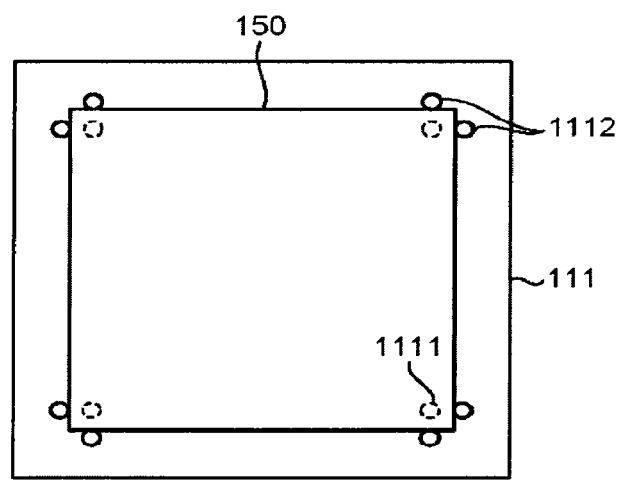

FIGS. 2A to 2C are exploded views showing the basic configuration of the mask casing. FIGS. 3A to 3C are views schematically showing an example of the configuration of an inner pod. FIG. 3A is a side view, FIG. 3B is a top view, and FIG. 3C is a top view in a state with a mask mounted thereon. The mask casing 100 has a dual pod structure composed of an inner pod 110 and an outer pod 120.

The inner pod 110 includes a base portion 111 and a cover portion 112, which serve to house a mask 150. The base portion 111 includes support members 1111 for supporting the mask 150, and guide members 1112 for preventing the mask 150 supported by the support members 1111 from causing lateral slippage. The support members 1111 are disposed near the four corners of the mask 150 having a rectangular shape, for example. The support members 1111 are formed of spherical members, for example, so as not to damage the mask 150. Further, the base portion 111 is formed with a purge gas supply port (not shown).

The cover portion 112 is provided with filters 1121 for exhausting the purge gas. The cover portion 112 has a recess at the region where the mask 150 is placed, and cuts off the communication between the inside and outside of the inner pod 110 when it covers the base portion 111.

The outer pod 120 includes a base portion 121 and a cover portion 122, which serve to house the inner pod 110. The base portion 121 includes support members 1211 for supporting the inner pod 110 and a purge gas supply port (not shown). The cover portion 122 is formed with a gas exhaust port (not shown). Further, the cover portion 122 has a recess at the region where the inner pod 110 is placed, and cuts off the communication between the inside and outside of the outer pod 120 when it covers the base portion 121.

Next, a storing method of the mask 150 in the mask casing 100 will be explained. At first, as shown in FIGS. 2A and 2B and FIGS. 3A and 3C, the mask 150 is placed at a predetermined position on the base portion 111 of the inner pod 110, and is then covered by the cover portion 112. In this state, the inside of the inner pod 110 is blocked off from the outside. Thereafter, as shown in FIG. 2C, the inner pod 110 is placed at a predetermined position on the base portion 121 of the outer pod 120, and is then covered by the cover portion 122. In this state, the inside of the outer pod 120 is blocked off from the outside. In this way, this dual structure is used, so that particles 51 can be hardly deposited onto the mask 150 while the mask 150 is stored. Here, the particle measurement mask 10 is formed in the same size as the product mask, it can be stored in this mask casing 100.

Figure 4:
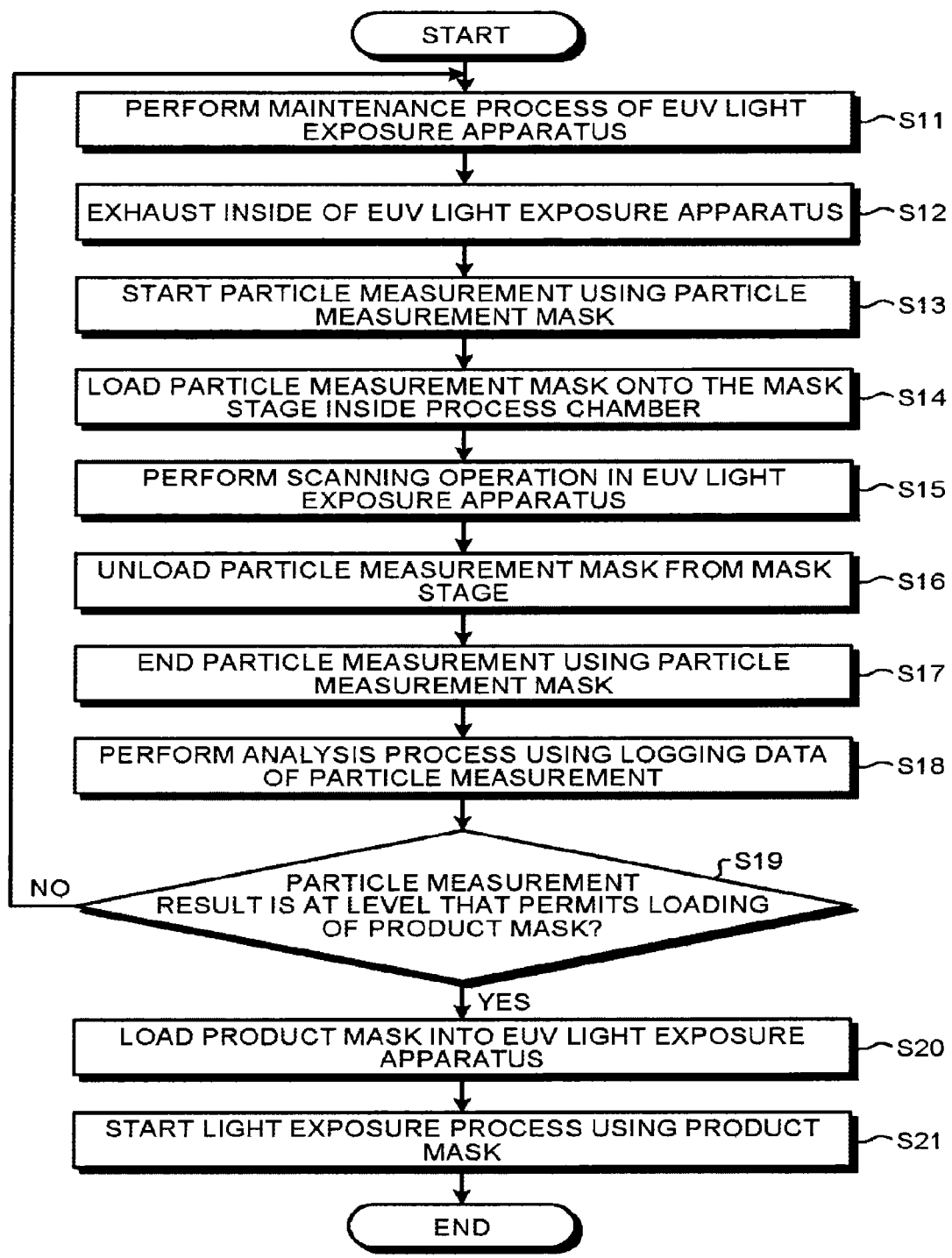
FIG. 4 is a flow chart showing an example of the sequence of a particle managing method according to the first embodiment.
Figure 5:
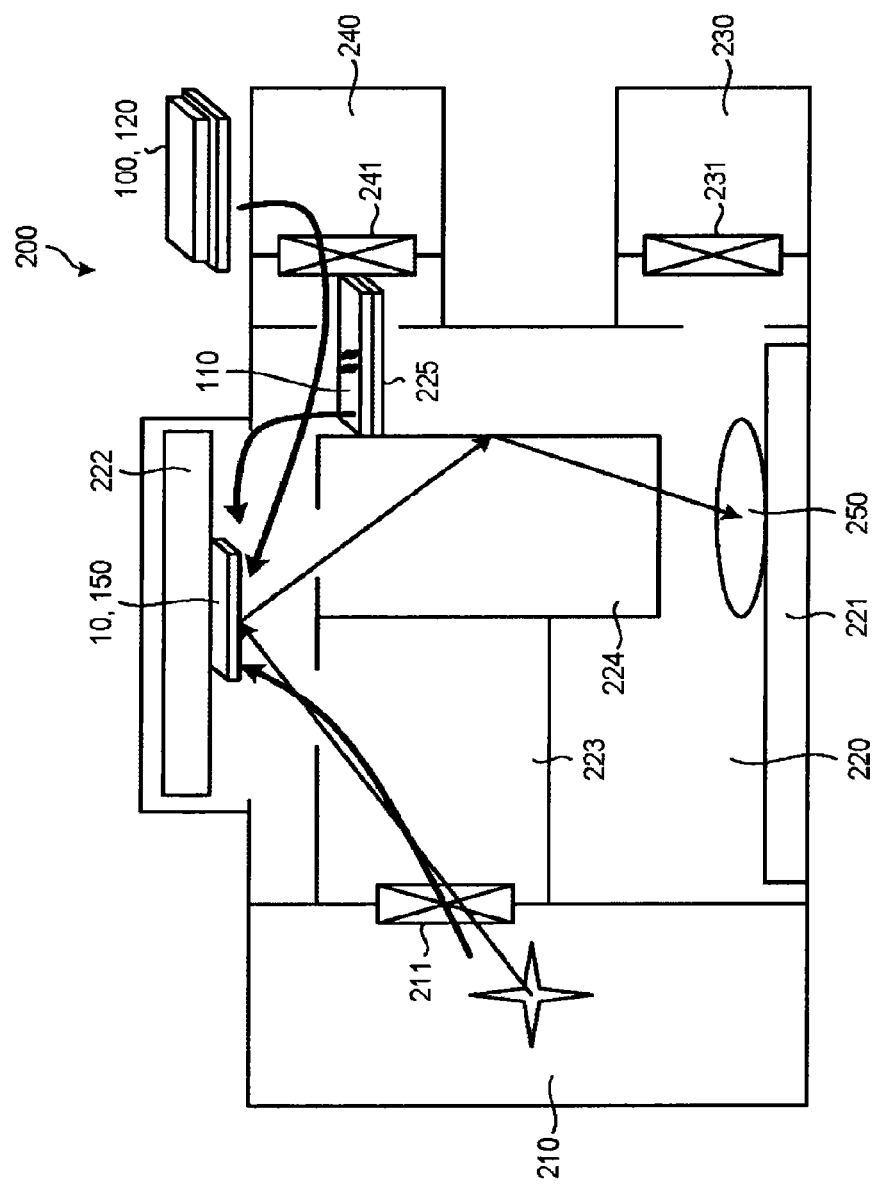
FIG. 5 is a view showing an example of the configuration of an EUV light exposure apparatus, to which the particle managing method is applied.

FIG. 4 is a flow chart showing an example of the sequence of a particle managing method according to the first embodiment. FIG. 5 is a view showing an example of the configuration of an EUV light exposure apparatus, to which the particle managing method is applied. The EUV light exposure apparatus 200 includes a light source 210, a process chamber 220, a wafer load lock chamber 230, and a mask load lock chamber 240. The inside of each of the light source 210, the process chamber 220, the wafer load lock chamber 230, and the mask load lock chamber 240 is exhausted by a vacuum pump, and is set at a predetermined vacuum level.

The light source 210 generates EUV light to be used for a light exposure process, and emits the EUV light to the process chamber 220. Between the light source 210 and the process chamber 220, a gate valve 211 is disposed, for example. When the light exposure process is performed, the gate valve 211 is opened, and the EUV light is guided into the process chamber 220.

The process chamber 220 defines a space for performing the light exposure process. Inside the process chamber 220, there is disposed a wafer stage 221 for holding a wafer 250 as a processing object, a mask stage 222 for holding the mask 150, an illumination optical system 223 for guiding the EUV light from the light source 210 to the mask 150, a projection optical system 224 for guiding the EUV light reflected from the mask 150 onto the wafer 250, and a buffer 225 for holding the inner pod 110 transferred from the mask load lock chamber 240.

The wafer load lock chamber 230 serves as a relay chamber for transferring the wafer 250 between the outside of the EUV light exposure apparatus 200 and the process chamber 220. Between the wafer load lock chamber 230 and the process chamber 220, a gate valve 231 is disposed.

The mask load lock chamber 240 serves as a relay chamber for transferring the mask 150 between the outside of the EUV light exposure apparatus 200 and the process chamber 220. Between the mask load lock chamber 240 and the process chamber 220, a gate valve 241 is disposed.

After the light exposure process is performed in the EUV light exposure apparatus 200 described above, a maintenance process of the EUV light exposure apparatus 200 is performed (step S11). For example, when a predetermined time has elapsed since the last maintenance, or when a signal indicating an abnormality is output from the apparatus, the maintenance process is performed in response to this event. In the maintenance process, the light source 210, the process chamber 220, the wafer load lock chamber 230, and the mask load lock chamber 240 are opened to the atmosphere, and replacement, cleaning, and/or adjustment of their inner components are performed.

After the maintenance process is finished, the inside of each of the light source 210, the process chamber 220, the wafer load lock chamber 230, and the mask load lock chamber 240 is exhausted (step S12). At this time, the mask casing 100 housing the particle measurement mask 10 is transferred to a load port of the EUV light exposure apparatus 200. Then, particle measurement using the particle measurement mask 10 is started (step S13). For example, the starting of the particle measurement may be performed by turning on the power supply 45 provided on the particle measurement mask 10, or may be performed by transmitting a start signal from a wireless communication unit (not shown) to the light emitting element 41, the light receiving element 42, the acceleration measurement unit 43, and the logging unit 44.

Then, the particle measurement mask 10 is loaded through the mask load lock chamber 240 onto the mask stage 222 inside the process chamber 220 (step S14). More specifically, the mask load lock chamber 240 is set to the atmospheric pressure, the inner pod 110 is taken out from the outer pod 120 of the mask casing 100 at the load port, and the inner pod 110 is transferred into the mask load lock chamber 240. Thereafter, the inside of the mask load lock chamber 240 is exhausted until it reaches a predetermined pressure. Then, the gate valve 241 is opened, and the inner pod 110 of the mask casing 100 is transferred onto the buffer 225 inside the process chamber 220. Thereafter, the gate valve 241 is closed, and the inside of the process chamber 220 is set to a predetermined vacuum level.

Then, the inner pod 110 is transferred by a transfer arm (not shown) from the buffer 225 to near the mask stage 222. Thereafter, the cover portion 112 of the inner pod 110 is detached, and the base portion 111 of the inner pod 110 is placed near the mask stage 222 by a transfer arm (not shown). More specifically, the base portion 111 is placed such that the particle measurement mask 10 on the base portion 111 faces the mask stage 222 with a predetermined distance between them. Thereafter, the particle measurement mask 10 is attracted and fixed to the mask stage 222 by an electrostatic force of the mask stage 222.

Thereafter, a scanning operation is performed in the EUV light exposure apparatus 200 (step S15). This scanning operation is performed by scanning with the particle measurement mask 10 in a scanning direction, as performed actually in the light exposure process. The scanning operation may be a simple scanning operation unaccompanied by irradiation with the EUV light, or may be a scanning operation accompanied by irradiation with the EUV light, which can be called a light exposure process.

Then, the particle measurement mask 10 is unloaded from the mask stage 222 and recovered (step S16). More specifically, the base portion 111 of the inner pod 110 is placed to face the mask stage 222 with a predetermined distance therebetween, and the particle measurement mask 10 is detached from the mask stage 222 and placed onto the base portion 111. Thereafter, the cover portion 112 of the inner pod 110 is put to cover the base portion 111, and the inner pod 110 is transferred to the buffer 225 by a transfer arm (not shown). Thereafter, the gate valve 241 is opened, and the inner pod 110 is transferred into the mask load lock chamber 240. After the gate valve 241 is closed, the inside of the mask load lock chamber 240 is set to the atmospheric pressure, and the inner pod 110 is transferred from inside the mask load lock chamber 240 to the outer pod 120 at the load port. Then, the inner pod 110 is housed in the outer pod 120. Consequently, the particle measurement mask 10 is recovered. Then, the particle measurement using the particle measurement mask 10 is ended (step S17). For example, the ending of the particle measurement may be performed by turning off the power supply 45 provided on the particle measurement mask 10, or may be performed by transmitting an end signal from a wireless communication unit (not shown) to the light emitting element 41, the light receiving element 42, the acceleration measurement unit 43, and the logging unit 44.

Thereafter, an analysis process is performed by use of logging data of the particle measurement collected by the logging unit 44 (step S18). For example, this analysis process is performed in a state where the logging unit 44 is detached from the particle measurement mask 10 and is connected to an information processing terminal, such as a personal computer, through an adaptor. Then, the information processing terminal reads the logging data inside the logging unit 44, and thereby creates a detected situation of particles 51. The detected situation of particles 51 is output to a display unit of the information processing terminal, for example.

Figure 6:
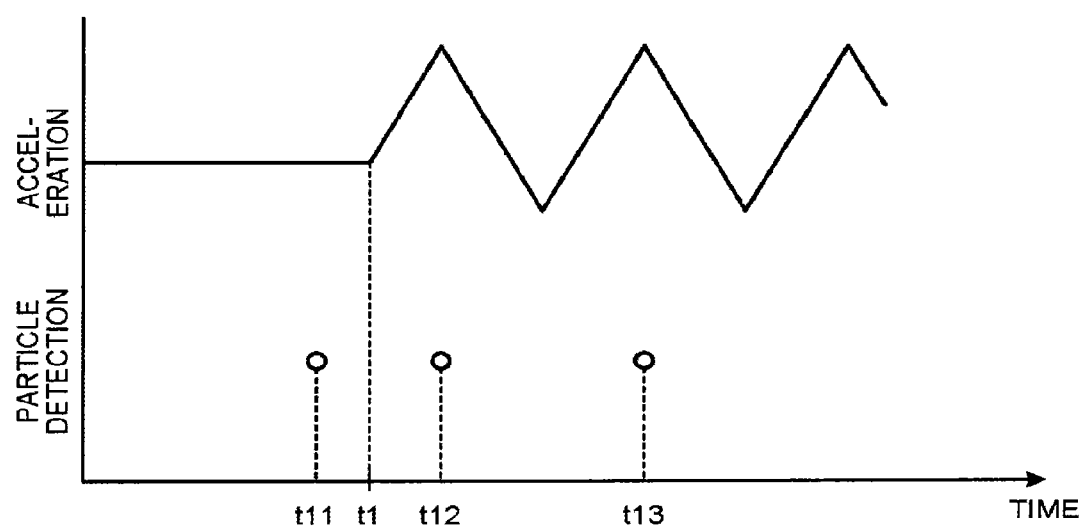
FIG. 6 is a view schematically showing an example of a particle measurement result according to the first embodiment.

FIG. 6 is a view schematically showing an example of a particle measurement result according to the first embodiment. FIG. 6 shows the relationship between an acceleration value and a particle discovery time. More specifically, the horizontal axis denotes the elapsed time from starting the particle measurement, and the vertical axis denotes the acceleration degree. Further, in this graph, an white circle "CD" indicates a time of detecting particles 51. From the measurement start to the time point t1, there is no acceleration generated. This represents a state where the particle measurement mask 10 was transferred from the load port to the mask stage 222. Thereafter, from the time point t1, the acceleration periodically repeats an increase and a decrease. This represents a state where the particle measurement mask 10 was being subjected to the scanning operation.

FIG. 6 shows that, under this situation, particles 51 were detected at time points t11, t12, and t13. The time point t11 indicates that particles 51 were generated in the middle of transfer to the mask stage 222. Further, the time points t12 and t13 indicate that particles 51 were being suspended during the scanning operation, i.e., during the light exposure operation. Further, the time points t12 and t13 indicate generation of particles 51 at positions with the same mountain shape periodically repeated, and so the position of a generation source of particles 51 can be specified.

As described above, based on the particle measurement result, it becomes possible to specify a generation frequency of particles 51 and/or a generation source of particles 51.

Thereafter, a judgment is made as to whether or not the particle measurement result is at a level that permits loading of the product mask (step S19). If the result is not at the level that permits loading of the product mask (No in the step S19), the sequence returns to the step S11, and the maintenance process of the EUV light exposure apparatus 200 is performed again. In this case, a position that seems to correspond to a particle generation source can be specified from the particle measurement result, and so the maintenance process can be performed at and around the particle generation source.

On the other hand, if the result is at the level that permits loading of the product mask (Yes in the step S19), the product mask is loaded into the EUV light exposure apparatus 200 (step S20), and the light exposure process is started (step S21). As a result, the particle managing method is completed.

Here, in the example described above, the measurement of particles 51 is performed, while the mask casing 100 is transferred from the load port into the EUV light exposure apparatus 200, then the scanning operation is performed, and then the mask casing 100 is transferred to the load port outside the EUV light exposure apparatus 200. However, particle measurement may be performed when the mask casing 100 containing the particle measurement mask 10 is housed into a mask stocker and stored therein. In this case, when the mask casing 100 is housed into the mask stocker, acceleration and deceleration operations take place, and so a detected situation of particles can be confirmed at these timings.

According to the first embodiment, the particle measurement mask 10 having the same size as the product mask 150 is provided with the particle measurement mechanism. Further, after a maintenance process of the light exposure apparatus is performed, particle measurement is performed, while the particle measurement mask 10 is transferred from outside the light exposure apparatus onto the mask stage 222 inside the light exposure apparatus, then the scanning operation is performed, and then the particle measurement mask 10 is transferred to outside the light exposure apparatus. Then, based on the particle measurement result, a judgment is made as to whether the inside of the process chamber 220 has an environment that permits use of the product mask. As a result, it is possible to detect particles 51 having intruded from outside the particle measurement mask 10, while the particle measurement mask 10 is transferred, or while the particle measurement mask 10 is clamped on the mask stage 222.

Further, the particle measurement result is stored in the logging unit 44, and is compared with an operation log in a light exposure state, i.e., the scanning operation, so that the particle detection timing can be collated with the traveling position of the particle measurement mask 10 inside the light exposure apparatus. As a result, it is also possible to easily find a cause of generating particles 51 inside the light exposure apparatus.

Further, the particle detecting period can be collated with the mask scanning operation period inside the light exposure apparatus, so that it is also possible to easily find a cause of generating particles. Further, it is possible to reduce such a problem that the product mask is loaded into the process chamber 220 of the light exposure apparatus when a large number of suspended particles are present inside the process chamber 220, and particularly near the mask stage 222. In other word, it is possible to reduce the risk of particle deposition onto the product mask inside the process chamber 220 of the light exposure apparatus. As a result, it is possible to reduce the mask cleaning frequency, and improve the semiconductor product yield.

Second Embodiment

In the second embodiment, an explanation will be given of another configuration example of a particle measurement mask usable to perform particle measurement inside the mask casing and inside the light exposure apparatus during the scanning operation, as in the first embodiment.

Figure 7A:
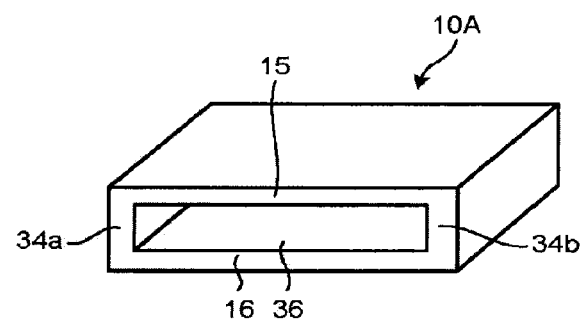
FIGS. 7A to 7C are views schematically showing an example of the configuration of a particle measurement mask according to a second embodiment.
Figure 7B:
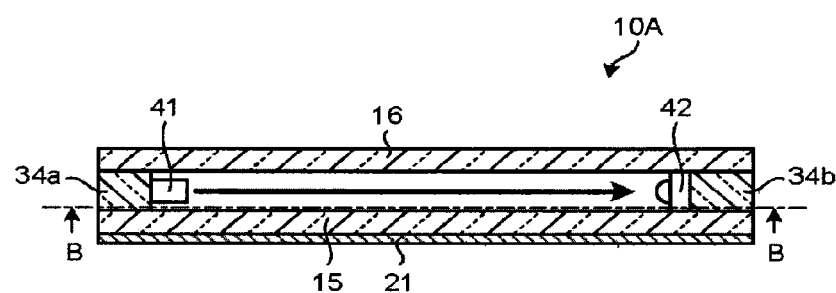
Figure 7C:
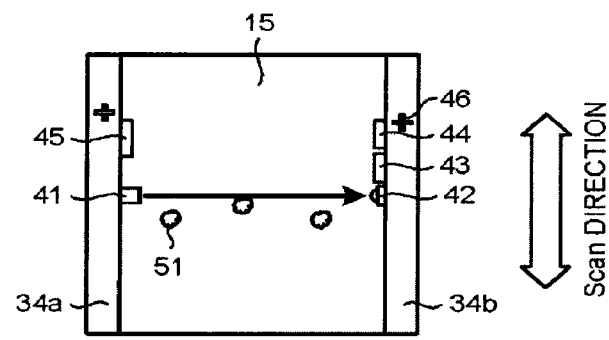

FIGS. 7A to 7C are views schematically showing an example of the configuration of a particle measurement mask according to the second embodiment. FIG. 7A shows a perspective view, FIG. 7B is a side view, and FIG. 7C is a sectional view taken along a line B-B of FIG. 7B. The particle measurement mask 10A according to the second embodiment includes a first mask substrate 15 forming the rear face, a second mask substrate 16 forming the front face, and support members 34a and 34b connecting between the first mask substrate 15 and the second mask substrate 16. Each of the first mask substrate 15 and the second mask substrate 16 is formed of a rectangular material having properties of a low thermal expansion coefficient and high flatness, such as a glass substrate.

The rear face of the first mask substrate 15 is provided with an electrostatic chuck conductive film 21 formed of a CrN film or the like. The front face of the second mask substrate 16 is formed with a pattern to be transferred onto a processing object. This pattern is the same as that explained in the first embodiment, and so its description will be omitted.

The support members 34a and 34b are disposed along the opposite ends of the front face of the first mask substrate 15 in directions perpendicular to the mask scanning direction. Thus, the support members 34a and 34b extend in directions parallel with the mask scanning direction. The front face of the first mask substrate 15 is connected to the rear face of the second mask substrate 16 by the support members 34a and 34b, so that it faces the rear face of the second mask substrate 16. Here, in the example described above, the first mask substrate 15, the second mask substrate 16, and the support members 34a and 34b are respectively formed of different members, and are connected to each other to constitute the particle measurement mask 10A, but this structure is not limiting. For example, a glass substrate having the appearance shown in FIG. 7A may be prepared, and then processed, so that the particle measurement mask 10A having the structure shown in FIG. 7A is constituted. Alternatively, a member composed of the first mask substrate 15 integrally formed with the support members 34a and 34b may be connected to the second mask substrate 16, so that the particle measurement mask 10A is constituted. Alternatively, a member composed of the second mask substrate 16 integrally formed with the support members 34a and 34b may be connected to the first mask substrate 15, so that the particle measurement mask 10A is constituted.

The inner surfaces of the support members 34a and 34b are provided with a mechanism that can detect particles 51 and is composed of a light emitting element 41, a light receiving element 42, an acceleration measurement unit 43, a logging unit 44, and a power supply 45, as described in the first embodiment. These members have the same functions as those explained in the first embodiment, and are arranged in the same way as in the first embodiment, and so their description will be omitted. Further, in the second embodiment, the space surrounded by the first mask substrate 15, the second mask substrate 16, and the support members 34a and 34b serves as a space that can detect particles 51. Further, this space is formed with an opening 36 at an end in the scanning direction. This opening 36 can serve to catch suspended particles 51.

This particle measurement mask 10A also has the same size as the product mask. Accordingly, the particle measurement mask 10A can be housed in the mask casing 100 shown in FIGS. 2A to 2C.

Further, this particle measurement mask 10A is fixed onto the mask stage 222 of the EUV light exposure apparatus 200, such that the extending directions of the support members 34a and 34b are in parallel with the scanning direction.

Here, a particle managing method using this particle measurement mask 10A is the same as that of the first embodiment, and so its description will be omitted.

The second embodiment can provide the same effects as the first embodiment.

Third Embodiment

In the first and second embodiments, an explanation has been given of a particle measurement mask usable to perform particle measurement during the scanning operation in the light exposure apparatus. In the third embodiment, an explanation will be given of a particle measurement mask and a particle managing method, which are usable to perform particle measurement inside the mask casing.

Figure 8:
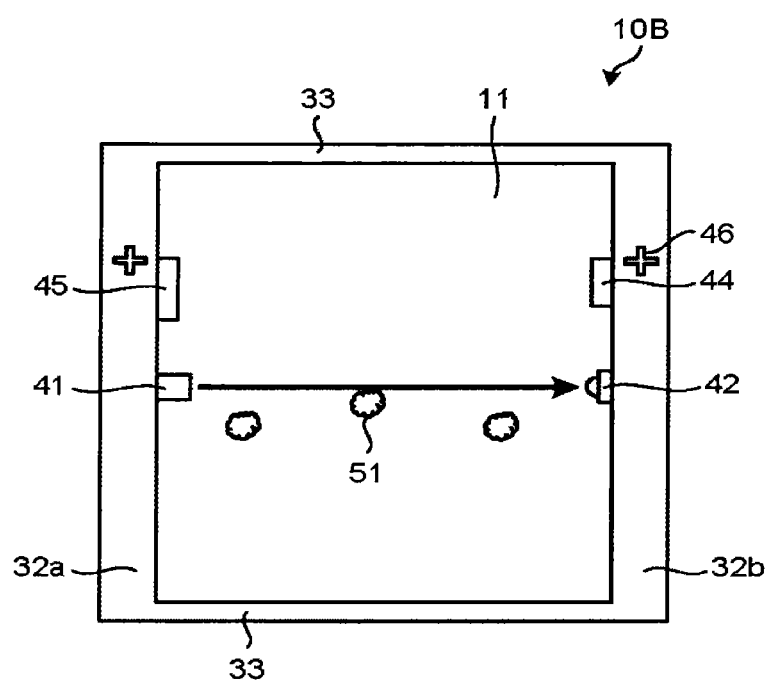
FIG. 8 is a top view schematically showing an example of the configuration of a particle measurement mask according to a third embodiment.

FIG. 8 is a top view schematically showing an example of the configuration of a particle measurement mask according to the third embodiment. The particle measurement mask 10B according to the third embodiment has a configuration designed by excluding the acceleration measurement unit 43 from the particle measurement mask 10 according to the first embodiment. Here, the other components of the configuration are the same as those of the first embodiment, and so their description will be omitted. Further, FIG. 8 omits illustration of the pattern shown in FIG. 1B.

The particle measurement mask 10B having this configuration can perform particle measurement when it is housed in the mask casing 100.

Figure 9:
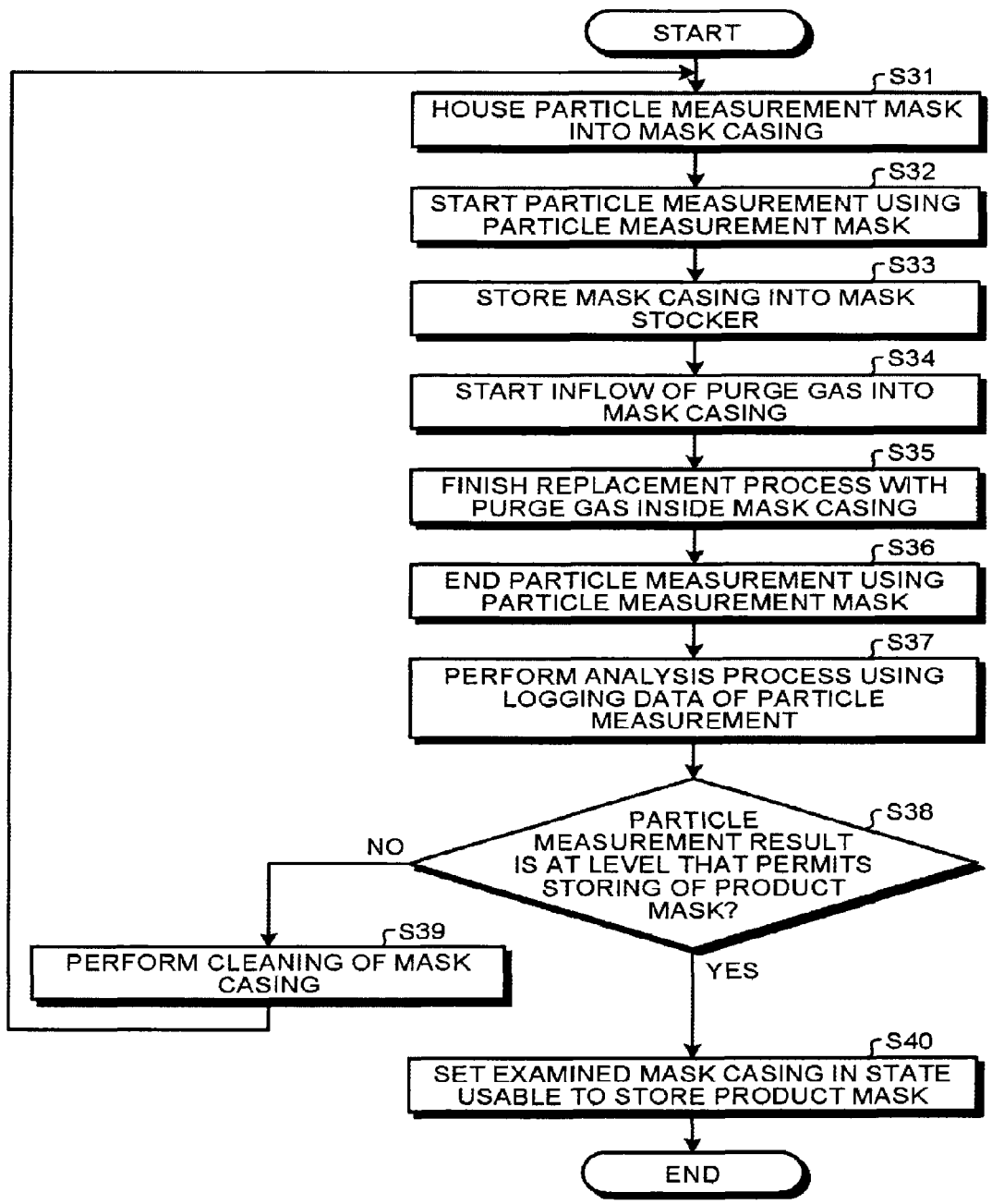
FIG. 9 is a flow chart showing an example of the sequence of a particle managing method according to the third embodiment.

Next, an explanation will be given of a particle managing method according to the third embodiment. FIG. 9 is a flow chart showing an example of the sequence of a particle managing method according to the third embodiment. At first, the particle measurement mask 10B is housed into the mask casing 100 (step S31). The mask casing 100 used here may have the structure shown in FIGS. 2A to 2C.

Then, particle measurement using the particle measurement mask 10B is started (step S32). For example, the starting of the particle measurement may be performed by turning on the power supply 45 provided on the particle measurement mask 10B, or may be performed by transmitting a start signal from a wireless communication unit (not shown) to the light emitting element 41, the light receiving element 42, and the logging unit 44.

Thereafter, the mask casing 100 is stored into a mask stocker (not shown) (step S33). The mask stocker is the original storing place for the mask casing 100 housing the product mask. Then, inflow of a purge gas into the mask casing 100 is started (step S34). As the purge gas, dry air or the like may be used.

When a predetermined time has elapsed, a replacement process with the purge gas inside the mask casing 100 is finished (step S35). The period of the inflow of the purge gas until the end of the replacement may be two hours, for example. Then, the particle measurement using the particle measurement mask 10B is ended (step S36). For example, the ending of the particle measurement may be performed by turning off the power supply 45 provided on the particle measurement mask 10B, or may be performed by transmitting an end signal from a wireless communication unit (not shown) to the light emitting element 41, the light receiving element 42, and the logging unit 44.

Then, an analysis process is performed by use of logging data of the particle measurement collected by the logging unit 44 (step S37). For example, this analysis process is performed in a state where the logging unit 44 is detached from the particle measurement mask 10B and is connected to an information processing terminal, such as a personal computer, through an adaptor. Then, the information processing terminal reads the logging data inside the logging unit 44, and thereby creates a detected situation of particles 51.

Thereafter, a judgment is made as to whether or not the particle measurement result is at a level that permits storing of the product mask into the mask casing 100 (step S38). If the result is not at the level that permits storing of the product mask (No in the step S38), cleaning of the mask casing 100 is performed (step S39), and the sequence returns to the step S31.

On the other hand, if the result is at the level that permits storing of the product mask (Yes in the step S38), the examined mask casing 100 is set in a state usable to store the product mask (step S40), and the sequence is completed.

Here, the explanation described above has taken as an example the particle measurement mask 10B having a structure excluding the acceleration measurement unit 43 from the particle measurement mask 10 according to the first embodiment. However, alternatively, the particle measurement mask used here may have a structure excluding the acceleration measurement unit 43 from the particle measurement mask 10A according to the second embodiment.

According to the third embodiment, the particle measurement mask 10B having the same size as the product mask is provided with the particle measurement mechanism. Further, when the particle measurement mask 10B is put in the mask casing 100, and is stored in the mask stocker, particle measurement is performed. Then, based on the particle measurement result, a judgment is made as to whether the inside of the mask casing 100 has an environment that permits storing of the product mask. Consequently, the mask casing 100, which is high in use frequency and low in cleaning frequency, can be confirmed in terms of a situation of particles suspended during gas purge. As a result, there is provided an effect capable of finding out a cleaning timing of the mask casing 100, and thereby it is possible to reduce the risk of particle deposition onto the product mask.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A particle measurement mask comprising:
    a first mask substrate;
    a support member arranged at a peripheral edge portion of a second main face of the first mask substrate, which is opposite to a first main face of the first mask substrate to come into contact with a mask stage; and
    a particle measurement unit arranged on a side surface of the support member, and configured to measure presence and absence of particles near the second main face.

2. The particle measurement mask according to claim 1, wherein the support member includes a first support portion and a second support portion, which are arranged at opposite end portions of the first mask substrate in a direction perpendicular to a scanning direction of the particle measurement mask in a light exposure apparatus, and extend in directions parallel with the scanning direction, and
    the particle measurement unit is disposed on the first support portion and the second support portion.

3. The particle measurement mask according to claim 2, wherein the particle measurement unit includes
    a particle detection unit configured to detect particles passing over the second main face of the first mask substrate, and
    a logging unit configured to log presence and absence of particles detected by the particle detection unit.

4. The particle measurement mask according to claim 3, wherein the particle detection unit includes a light emitting element and a light receiving element configured to measure a received light intensity of light emitted from the light emitting element.

5. The particle measurement mask according to claim 4, wherein the light emitting element is formed of a laser diode or LED.

6. The particle measurement mask according to claim 4, wherein the light emitting element is disposed on the first support portion, and
    the light receiving element is disposed on the second support portion at a position facing the light emitting element.

7. The particle measurement mask according to claim 3, wherein the particle measurement unit further includes an acceleration measurement unit configured to measure acceleration applied to the particle measurement mask, and
    the logging unit is configured to further log acceleration measured by the acceleration measurement unit.

8. The particle measurement mask according to claim 2, wherein a pattern is arranged on the second main face of the first mask substrate.

9. The particle measurement mask according to claim 8, wherein an alignment mark usable by the light exposure apparatus is further arranged on the second main face of the first mask substrate.

10. The particle measurement mask according to claim 2, wherein the support member further includes a third support portion and a fourth support portion, which are arranged at opposite end portions of the first mask substrate in a direction parallel with the scanning direction, and extend in directions perpendicular to the scanning direction, and the support member is formed in a frame shape on the peripheral edge portion of the first mask substrate.

11. The particle measurement mask according to claim 2, further comprising a second mask substrate arranged on the support member.

12. The particle measurement mask according to claim 11, wherein a pattern is arranged on a third main face of the second mask substrate, which does not face the first mask substrate.

13. The particle measurement mask according to claim 12, wherein an alignment mark usable by the light exposure apparatus is further arranged on the third main face of the second mask substrate.

14. The particle measurement mask according to claim 1, wherein a conductive film is arranged on the first main face of the first mask substrate.

15. A particle managing method comprising:
performing a maintenance process of a light exposure apparatus;
housing a particle measurement mask into a mask casing, the particle measurement mask including a particle measurement unit arranged on a second main face of a mask substrate, which is opposite to a first main face of the mask substrate to come into contact with a mask stage of the light exposure apparatus, and configured to perform particle measurement, which includes detection of particles and measurement of acceleration applied to the particle measurement mask;
starting the particle measurement using the particle measurement unit, after performing the maintenance process of the light exposure apparatus;
transferring the mask casing from outside the light exposure apparatus into the light exposure apparatus;
transferring the particle measurement mask from inside the light exposure apparatus onto the mask stage;
transferring the particle measurement mask from the mask stage into the mask casing;
transferring the mask casing from inside the light exposure apparatus to outside the light exposure apparatus;
ending the particle measurement using the particle measurement unit;
creating a detected situation of particles inside the light exposure apparatus, based on a result of the particle measurement; and
making a judgment as to whether the light exposure apparatus is in a state that permits loading of a product mask, by use of the detected situation of particles, wherein
in a period of from the starting to the ending of the particle measurement, the particle measurement unit logs presence and absence of particle detection, and measure the acceleration at predetermined time intervals.

16. The particle managing method according to claim 15, further comprising:
loading the product mask into the light exposure apparatus, if the light exposure apparatus is in a state that permits loading of the product mask; and
returning to the performing of the maintenance process, if the light exposure apparatus is in a state that does not permit loading of the product mask.

17. The particle managing method according to claim 15, further comprising:
performing a scanning operation of the mask stage with the particle measurement mask attached thereto, after the transferring of the particle measurement mask onto the mask stage, and before the transferring of the particle measurement mask into the mask casing;
making the judgment while specifying, by use of the detected situation of particles, a position of generating the particles inside the light exposure apparatus; and
performing the maintenance process at and around the position of generating the particles thus specified, if the light exposure apparatus is in a state that does not permit loading of the product mask.

18. The particle managing method according to claim 15, wherein the mask casing includes an inner pod configured to house the particle measurement mask, and an outer pod configured to house the inner pod,
in the transferring of the mask casing into the light exposure apparatus, the inner pod is taken from the outer pod and transferred into the light exposure apparatus, and
in the transferring of the particle measurement mask onto the mask stage, the particle measurement mask is taken from the inner pod and transferred onto the mask stage.

19. A particle managing method comprising:
housing a particle measurement mask into a mask casing, the particle measurement mask including a particle measurement unit arranged on a second main face of a mask substrate, which is opposite to a first main face of the mask substrate to come into contact with a mask stage of the light exposure apparatus, and configured to perform particle measurement;
starting the particle measurement using the particle measurement unit;
storing the mask casing into a mask stocker;
supplying a purge gas into the mask casing for a predetermined time;
ending the particle measurement using the particle measurement unit;
creating a detected situation of particles inside the mask casing, based on a result of the particle measurement; and
making a judgment as to whether the mask casing is in a state that permits storing of a product mask, by use of the detected situation of particles, wherein
in a period of from the starting to the ending of the particle measurement, the particle measurement unit logs presence and absence of particle detection.

20. The particle managing method according to claim 19, wherein the mask casing includes an inner pod configured to house the particle measurement mask, and an outer pod configured to house the inner pod.

* * * * *